(12) United States Patent
Aletru et al.

(10) Patent No.: US 7,897,773 B2
(45) Date of Patent: Mar. 1, 2011

(54) UREA DERIVATIVES OF TROPANE, THEIR PREPARATION AND THEIR THERAPEUTIC APPLICATION

(75) Inventors: Michel Aletru, Antony (FR); Alain Jean Braun, Antony (FR); Claudie Namane, Antony (FR); Olivier Venier, Antony (FR); Christophe Philippo, Antony (FR); Patrick Mougenot, Antony (FR); Eric Nicolai, Antony (FR); Stefan Gussregen, Wiesbaden (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/332,547

(22) Filed: Dec. 11, 2008

(65) Prior Publication Data
US 2009/0170894 A1 Jul. 2, 2009

Related U.S. Application Data

(63) Continuation of application No. PCT/FR2007/001070, filed on Jun. 26, 2007.

(30) Foreign Application Priority Data

Jun. 27, 2006 (FR) .................................. 06 05785
Jan. 25, 2007 (FR) .................................. 07 00507

(51) Int. Cl.
C07D 401/00 (2006.01)
(52) U.S. Cl. .......................................................... 546/126
(58) Field of Classification Search .................... 546/126
See application file for complete search history.

(56) References Cited

FOREIGN PATENT DOCUMENTS

| EP | 0130795 | 1/1985 |
|---|---|---|
| EP | 1283199 | 2/2003 |
| WO | WO 92/22552 | 12/1992 |
| WO | WO 03/031436 | 4/2003 |
| WO | 03/106456 | 12/2003 |
| WO | WO 2004/033427 | 4/2004 |
| WO | 2004/089896 | 10/2004 |
| WO | WO 2005/047250 | 5/2005 |
| WO | WO 2006/053024 | 5/2006 |
| WO | WO 2006/055752 | 5/2006 |
| WO | WO 2006/105127 | 10/2006 |
| WO | WO 2006/132436 | 12/2006 |

OTHER PUBLICATIONS

West, Anthony Solid State Chemistry and its applications, John Wiley & Sons 1984, p. 358.*
Dorwald F. A. Side Reactions in Organic Synthesis, 2005, Wiley: VCH, Weinheim p. IX of Preface p. 1-15.*
Andrews, R. C., et. al., Effects of the 11B-Hydroxysteroid Dehydrogenase Inhibitor Carbenoxolone on Insulin Sensitivity in Men with Type 2 Diabetes, The Journal of Clinical Endocrinology & Metabolism, vol. 88, No. 1, pp. 285-291, (2003).
Barf, T. et. al., Arylsulfonamidothiazoles as a New Class of Potential Antidiabetic Drugs. Discovery of Potent and Selective Inhibitors of the 11 Beta-Hydroxysteroid Dehydrogenase Type 1, American Chemical Society, (2002), vol. 45, No. 18, pp. 3813-3815.
Buffat, M. G. P., et. al., Synthesis of Piperidines, Tetrahedron, vol. 60, (2004), pp. 1701-1709.
Cooper, M. S., et. al., Expression and Functional Consequences of 11B-Hydroxysteroid Dehydrogenase Activity In Human Bone, Bone, vol. 27, No. 3, (2000), pp. 375-381.
Coudert, G., et. al., A New Synthesis of 3,4-Dibhydro-2H-1, 4-Benzoxazines Using Solid-Liquid Phase-Transfer Catalysis, Synthesis, vol. 7, pp. 541-543, (1979).
Davani, B., et. al., Type 1 11B-Hydroxysteroid Dehydrogenase Mediates Glucocorticoid Activation and Insulin Release in Pancreatic Islets, The Journal of Biological Chemistry, vol. 275, No. 45, pp. 34841-34844, (2000).
Grzyb, J. A., et. al., Carbamoylimidazolium and Thiocarbamoylimidazolium Salts: Novel Reagents for the Synthesis of Ureas, Thioureas, Carbamates, Thiocarbamates and Amides, Tetrehedron 61, 30 (2005) pp. 7153-7175.
Hermanowski-Vosatka, A., et. al., 11B-HSD1 Inhibition Ameliorates Metabolic Syndrome and Prevents Progresion of Atherosclerosis in Mice, J. Exp. Med., vol. 202, pp. 517-527, (2005).
Kotelevtsev, Y., et. al., 11B-Hydroxysteroid Dehydrogenase Type 1 Knockout Mice Show Attenuated Glucocorticoid-Inducible Responses and Resist Hyperglycemia on Obesity or Stress, Proc. Natl. Acad. Sci. USA, vol. 94, pp. 14924-14929, (1997).
Kuwabe, S., et. al., Palladium-Catalyzed Intramolecular C-O Bond Formation, J. Am. Chem. Soc. (2001), vol. 123, pp. 12202-12206.
Laschat, S., et. al., Stereoselective Synthesis of Piperidines, Synthesis (2000), vol. 13, pp. 1781-1813.
Lupien, S. J., et. al., Cortisol Levels During Human Aging Predict Hippocampal Atrophy and Memory Deficits, Nat. Neurosci., vol. 1, pp. 69-73, (1998).
Masuzaki, H., et. al., A Transgenic Model of Visceral Obesity and The Metabolic Syndrome, Science, vol. 294, pp. 2166, (2001).
Masuzaki, H., et. al., Transgenic Amplification of Glucocorticoid Action in Adipose Tissue Causes High Blood Pressure in Mice, J. Clinical Invest., vol. 112, pp. 83-90, (2003).
Matsuzawa, Y., et. al., Molecular Mechanism of Metabolic Syndrome X: Contribution of Adipocytokines Adipocyte-derived Bioactive Substances, Acad. Sci. vol. 892, pp. 146-154, (1999).
McEwen, B. S., et. al., Stress and Cognitive Function, Curr. Opin. Neurobiol., vol. 5, pp. 205-216, (1995).

(Continued)

Primary Examiner — D. Margaret Seaman
Assistant Examiner — Nizal S Chandrakumar
(74) Attorney, Agent, or Firm — Jiang Lin

(57) ABSTRACT

The present invention is related to a compound of formula (I)

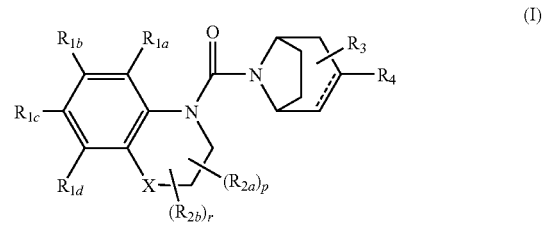

wherein $R_{1a}$, $R_{1b}$, $R_{1c}$, $R_{1d}$, $R_{2a}$, $R_{2b}$, $R_3$, $R_4$, p, r and ⎓⎓ are as defined herein, its preparation, pharmaceutical composition and use as a modulator of the activity of the 11β-hydroxysteroid dehydrogenase type 1 (11βHSD1).

9 Claims, No Drawings

OTHER PUBLICATIONS

Moisan, M-P., et. al., 11B-Hydroxysteroid Dehydrogenase Bioactivity and Messenger RNA Expression in Rat Forebrain: Localization in Hypothalamus, Hippocampus, and Cortex. Endocrinology, vol. 127, pp. 1450-1455, (1990).

Morton, N. M., et. al., Improved Lipid and Lipoprotein Profile, Hepatic Insulin Sensitivity, and Glucose Tolerance in 11B-Hydroxysteroid Dehydrogenase Type 1 Null Mice, J. Biol. Chem., vol. 276, pp. 41293-41300.

Rauz, S., et. al., Expression and Putative Role of 11B-Hydroxysteroid Dehydrogenase Isozymes within the Human Eye, Invest. Ophtamol. Vis. Sci., vol. 42, pp. 2037-2042, (2001).

Reaven, G. M., et. al., Role of Insulin Resistance in Human Disease (Syndrome X): An Expanded Definition, Ann. Rev. Med., vol. 44, pp. 121-134, (1993).

Rocha, B. A., et. al., 11beta-Hydroxsteroid Dehydrogenase Type 1 (11 beta-HSD1) Inhibition Prolonged Memory Retention in Mice, Abstract 231 ACS Meeting, Atlanta Mar. 26-30, 2006.

Sandeep, T. C., et. al., 11B-Hydrosteroid Dehydrogenase Inhibition Improves Cognitive Function in Healthy Elderly Men and Type 2 Diabetics, Proc. Natl. Acad. Sci., vol. 101, pp. 6734-6738, (2004).

Shankaran, K., et. al., Syntheses and SAR Studies of 4-(Heteroarylpiperdin-1-yl-Methyl)-Pyrrolidin-1-yl-Acetic Acid Antagonists of the Human CCR5 Chemokine Receptor, Bioorganic & Medicinal Chemistry Letters, vol. 14, (2004), pp. 3419-3424.

Stokes. J., et. al., Distribution of Glucorticoid and Mineralocorticoid Receptors and 11B-Hydroxysteroid Dehydrogenases in Human and Rat Ocular Tissues, Invest. Ophthalmol. Vis. Sci., vol. 41, pp. 1629-1638, (2000).

Terao, Y., et. al., Trifluoroacetic Acid-Catalyzed 1,3-Cycloaddition of the Simplest Iminium Ylide Leading to 3-or 3,4-Substituted Pyrrolidines and 2,5-Dihydropyrroles, Chem. Pharm. Bull. (1985), vol. 33, No. 7, pp. 2762-2766.

Tomlinson, J. W., et. al., 11B-Hydroxysteroid Dehydrogenase Type 1: A Tissue-Specific Regulator of Glucocorticoid Response, Endocrine Reviews, vol. 25, No. 3, pp. 831-866 (2004).

Wajchenberg, B. L., et. al., Subcutaneous and Visceral Adipose Tissue: Their Relation to the Metabolic Syndrome, Endocrine Reviews, vol. 21, No. 6, pp. 697-738, (2000).

Wang, S. J. Y., et. al., Inhibition of 11B-Hydroxysteroid Dehydrogenase Type1 Reduces Food Intake and Weight Gain but Maintains Energy Expenditure in Diet-Induced Obese Mice, Diabetologia, (2006), vol. 49, pp. 1333-1337.

Yau, J. L. W., et. al., Lack of Tissue Glucocorticoid Reactivation in 11B-Hydroxysteroid Dehydrogenase Type 1 Knockout Mice Ameliorates Age-Related Learning Impairments, Proc. Natl. Acad. Sci., vol. 98, pp. 4716-4721, (2001).

Lu, Z., et. al., Substituted Bridged Phenyl Piperidines: Orally Active Growth Hormone Secretagogues, Bioorganic & Medicinal Chemistry Letters, vol. 13, (2003), pp. 1817-1820.

Gilbert, A. M., et. al., Modulation of Selective Serotonin Reuptake Inhibitor and 5-HT1A Antagonist Activity in 8-Aza-Bicyclo[3.2.1.]Octane Derivatives of 2,3-Dihydro-1,4-Benzodioxane, Bioorganic & Medicinal Chemistry Letters, vol. 14, (2004), pp. 515-518.

Sikazwe, D. M. N., et. al., Haloperidol: Toward Further Understanding of the Structural Contributions of its Pharmacophoric Elements at D2-Like Receptors, Bioorganic & Medicinal Chemistry Letters, vol. 14, (2004), pp. 5739-5742.

* cited by examiner

UREA DERIVATIVES OF TROPANE, THEIR PREPARATION AND THEIR THERAPEUTIC APPLICATION

This application is a Continuation of International Application No. PCT/FR2007/001070, filed Jun. 26, 2007, which is incorporated herein by reference in its entirety.

FIELD OF THE INVENTION

The present invention relates to urea derivatives of tropane, to the preparation thereof and to the therapeutic use thereof. The present compounds modulate the activity of the 11β-hydroxysteroid dehydrogenase type 1 (11βHSD1) and are of use in the treatment of pathologies in which such a modulation is beneficial, as in the case of metabolic syndrome or non-insulin-dependant type 2 diabetes.

BACKGROUND OF THE INVENTION

11β-hydroxysteroid dehydrogenase type 1 (11βHSD1) locally catalyzes the conversion of inactive glucocorticoids (cortisone in humans) to active glucocorticoids (cortisol in humans) in various tissues and organs, mainly the liver and the adipose tissue, but also in the muscles, bones, pancreas, endothelium and ocular tissue and in certain parts of the central nervous system. 11βHSD1 acts as a regulator of glucocorticoid action in the tissues and organs where it is expressed (Tomlinson et al., *Endocrine Reviews* 25(5), 831-866 (2004, Davani et al., *J. Biol. Chem.* 275, 34841 (2000); Moisan et al., *Endocrinology,* 127, 1450 (1990)).

The most important pathologies in which glucocorticoids and the inhibition of 11βHSD1 are involved are indicated below.

A. Obesity, Type 2 Diabetes and Metabolic Syndrome

The role of 11βHSD1 in obesity, type 2 diabetes and metabolic syndrome (also known as syndrome X or insulin resistance syndrome), where the symptoms include visceral obesity, glucose intolerance, insulin resistance, hypertension, type 2 diabetes and hyperlipodemia (Reaven *Ann. Rev. Med.* 44, 121 (1993)) is described in many publications. In humans, treatment with carbenoxolone (a nonspecific inhibitor of 11βHSD1) improves insulin sensitivity in slim volunteer patients and in type 2 diabetics (Andrews et al., *J. Clin. Endocrinol. Metab.* 88, 285 (2003)). Furthermore, mice in which the 11βHSD1 gene has been knocked out are resistant to hyperglycemia induced by stress and obesity, show attenuated induction of liver neoglucogenesis enzymes (PEPCK and G6P) and exhibit an increased sensitivity to insulin in adipose tissue (Kotelevstev et al., *Proc Nat Acad. Sci.* 94, 14924 (1997); Morton et al., *J. Biol. Chem.* 275, 41293 (2001)). Moreover, transgenic mice in which the 11β-HSD1 gene has been overexpressed in adipose tissues exhibit a phenotype similar to that of human metabolic syndrome (Masuzaki et al., *Science* 294, 2166 (2001)). It should be noted that the phenotype observed exists without any increase in total circulating glucocorticoids, but is induced by the specific increase in active glucocorticoids in adipose deposits.

Moreover, new classes of specific 11βHSD1 inhibitors have recently emerged:

arylsulfonamidothiazoles have shown that they improve sensitivity to insulin and reduce the blood glucose level in mice exhibiting hyperglycemia (Barf et al., *J. Med. Chem.* 45, 3813 (2002)). Furthermore, in a recent study, it has been shown that compounds of this type reduce food intake and also weight gain in obese mice (Wang et al., *Diabetologia* 49, 1333 (2006));

triazoles have shown that they improve metabolic syndrome and slow down the progression of atherosclerosis in mice (Hermanowski-Vosatka et al., *J. Exp. Med.* 202, 517 (2005)).

B. Cognition and Dementia

Slight cognitive problems are common phenomena in elderly individuals and can, in the end, result in the progression of dementia. In the case of elderly humans just as in the case of aged animals, inter-individual differences for general cognitive functions have been linked to differences in long-term exposure to glucocorticoids (Lupien et al., *Nat. Neurosci.* 1, 69, (1998)). Moreover, dysregulation of the HPA (hypothalamic-pituitary-adrenal) axis resulting in chronic exposure of certain sub-regions of the brain to glucocorticoids has been proposed as contributing to the decline of cognitive functions (McEwen et al., *Curr. Opin. Neurobiol.* 5, 205, 1995). 11βHSD1 is abundant in the brain and is expressed in many sub-regions, including the hypothalamus, the frontal cortex and the cerebellum (Sandeep et al., *Proc. Natl. Acad. Sci.* 101, 6734 (2004)). Mice deficient in 11βHSD1 are protected against glucocorticoid-associated hypothalamic dysfunctions which are related to aging (Yau et al., *Proc. Natl. Acad. Sci.* 98, 4716, (2001)). Furthermore, in studies in humans, it has been shown that the administration of carbenoxolone improves verbal fluidity and verbal memory in elderly individuals (Yau et al., *Proc. Natl. Acad. Sci.* 98, 4716, (2001)), Sandeep et al., *Proc. Natl. Acad. Sci.* 101, 6734 (2004)). Finally, the use of selective 11βHSD1 inhibitors of triazole type has shown that they prolong memory retention in aged mice (Rocha et al., Abstract 231 ACS meeting, Atlanta, 25-30 Mar. 2006).

C. Intraocular Pressure

Glucocorticoids can be used topically or systemically for a large variety of pathologies of clinical opthalmology. One particular complication of these treatments is glaucoma induced by the use of corticosteroids. This pathology is characterized by elevated intraocular pressure (IOP). In the most serious cases and for non-treated forms, the IOP may result in a partial loss of visual field and possibly even complete loss of sight. The IOP is the result of an imbalance between the production of aqueous humor and the drainage thereof. The aqueous humor is produced in the non-pigmented epithelial cells and drainage is carried out through the cells of the trabecular network. 11βHSD1 is localized in the non-pigmented epithelial cells and its function is clearly the amplification of glucocorticoid activity in these cells (Stokes et al., *Invest. Opthalmol. Vis. Sci.* 41, 1629 (2000)). This notion is confirmed by the observation that the concentration of free cortisol is in great excess relative to cortisone in the aqueous humor (14/1 ratio). The functional activity of 11βHSD1 in the eyes has been evaluated by studying the action of carbenoxolone in normal volunteers. After seven days of treatment with carbenoxolone, the IOP is reduced by 18% (Rauz et al., *Invest. Ophthamol. Vis. Sci.* 42, 2037 (2001)). The inhibition of 11βHSD1 in the eyes is therefore predicted to reduce the local concentration of glucocorticoids and the IOP, producing a beneficial effect on the treatment of glaucoma and of other sight disorders.

D. Hypertension

Hypertensive substances derived from adipocytes such as leptin and angiotensinogen have been proposed as being key elements in obesity-related hypertension pathologies (Wajchenberg et al., *Endocr. Rev.* 21, 697 (2000)). Leptin, which is secreted in excess in transgenic aP2-11βHSD1 mice (Masuzaki et al., *J. Clinical Invest.* 112, 83 (2003)), can activate various networks of sympathetic neuronal systems, including those which regulate arterial pressure (Matsuzawa et al.,

*Acad. Sci.* 892, 146 (1999)). Furthermore, the renin-angiotensin system (RAS) has been identified as being a determining pathway in the variation of arterial pressure. Angiotensinogen which is produced in the liver and the adipose tissue, is a key substrate for renin and is responsible for activation of the RAS. The plasma angiotensinogen level is significantly elevated in transgenic aP2-11βHSD1 mice, as are those of angiotensin II and of aldosterone (Masuzaki et al., *J. Clinical Invest.* 112, 83 (2003)); these elements produce an elevated arterial pressure. The treatment of these mice with low doses of an angiotensin II receptor antagonist abolishes this hypertension (Masuzaki et al., *J. Clinical Invest.* 112, 83 (2003)). This information illustrates the importance of the local activation of glucocorticoids in adipose tissue and the liver, and suggests that this hypertension may be caused or exacerbated by the activity of 11βHSD1 in these tissues. The inhibition of 11βHSD1 and the reduction of the glucocorticoid level in adipose tissue and/or the liver is therefore predicted as having a beneficial role for the treatment of hypertension and of associated cardiovascular pathologies.

E. Osteoporosis

Skeletal development and bone functions are also regulated by the action of glucocorticoids. 11βHSD1 is present in osteoclasts and osteoblasts. The treatment of normal volunteers with carbenoxolone has shown a decrease in bone resorption markers without any change in bone formation markers (Cooper et al., Bone, 27, 375 (2000)). The inhibition of 11βHSD1 and the reduction of the glucocorticoid level in the bones could therefore be used as a mechanism of protection in the treatment of osteoporosis.

Urea derivatives of tropane which modulate 11βHSD1 activity have now been found.

SUMMARY OF THE INVENTION

The subject of the present invention is compounds corresponding to formula (I):

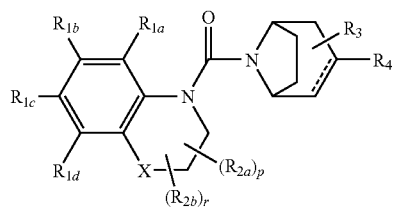

(I)

in which:
X represents either a carbon, oxygen, sulfur or nitrogen atom or the —$SO_2$— group;
the dashed-line bond is a single bond or a double bond;
$R_{1a,b,c,d}$ and $R_{2a,b}$ which may be identical or different, each represent a hydrogen or halogen atom; a ($C_1$-$C_5$)alkyl; ($C_1$-$C_5$)alkoxy; ($C_1$-$C_5$)haloalkyl, hydroxyl; hydroxy($C_1$-$C_5$)alkyl, ($C_1$-$C_5$)alkoxy ($C_1$-$C_5$)alkyl; or cyano group; a —$COOR_5$ group; an —$NR_6R_7$ group; a —$COOR_5$—($C_1$-$C_5$)alkyl group, an —$NR_6R_7$—($C_1$-$C_5$)alkyl group, a —$CONR_6R_7$ group, a —$CONR_6R_7$—($C_1$-$C_5$)alkyl group or an —$SO_2NR_6R_7$ group;
—($R_{2a}$)$_p$ or ($R_{2b}$)$_r$ may also form, with the carbon atom to which they are attached, a C=O group;
$R_3$ represents a hydrogen atom, a fluorine atom, a ($C_1$-$C_5$) alkyl; ($C_1$-$C_5$)alkoxy; alkoxy($C_1$-$C_5$)alkyl; hydroxyl; hydroxy($C_1$-$C_5$)alkyl; ($C_1$-$C_5$)haloalkyl; or cyano group; a —$COOR_5$ group; an —$NR_6R_7$ group; a —$COOR_5$—($C_1$-$C_5$)alkyl group, an —$NR_6R_7$—($C_1$-$C_5$)alkyl group, a —$CONR_6R_7$ group, or a —$CONR_6R_7$—($C_1$-$C_5$)alkyl group;

$R_4$ represents:
a hydrogen atom or a ($C_1$-$C_5$)alkyl group;
a ($C_3$-$C_6$)cycloalkyl group;
a heterocycle;
a monocyclic or bicyclic aryl group containing from 5 to 10 carbon atoms;
a monocyclic or bicyclic heteroaryl group containing from 2 to 9 carbon atoms;
the aryl or heteroaryl group being optionally substituted with 1 to 4 substituents chosen from halogen atoms and the groups: ($C_1$-$C_5$)alkyl; ($C_1$-$C_5$)alkoxy; ($C_1$-$C_5$)haloalkyl, hydroxyl; hydroxy($C_1$-$C_5$)alkyl, ($C_1$-$C_5$)alkoxy ($C_1$-$C_5$)alkyl; cyano; optionally substituted phenyl; optionally substituted benzyl; —$COOR_5$; —$NR_6R_7$; a —$COOR_5$—($C_1$-$C_5$)alkyl group, an —$NR_6R_7$—($C_1$-$C_5$)alkyl group, a —$CONR_6R_7$ group, a —$CONR_6R_7$—($C_1$-$C_5$)alkyl group, an —$SO_2NR_6R_7$ group, an —$NR_6$—$COR_5$ group;

p and r, which may be identical or different, are integers equal to 1 or 2;
$R_5$ represents a hydrogen atom, ($C_1$-$C_5$)alkyl group or a ($C_3$-$C_6$)cycloalkyl group;
$R_6$ and $R_7$, which may be identical or different, each represent a hydrogen atom, a ($C_1$-$C_5$)alkyl group; a ($C_3$-$C_6$) cycloalkyl group; a ($C_1$-$C_5$)alkylcarbonyl group; a hydroxymethyl($C_1$-$C_5$)alkyl group;
a ($C_1$-$C_5$)alkoxymethyl($C_1$-$C_5$)alkyl group; an aryl group or an —$SO_2$—$R_5$ group, or may form, together with the nitrogen atom to which they are attached, an optionally substituted heterocycle.

DETAILED DESCRIPTION OF THE INVENTION

The compounds of formula (I) may comprise one or more asymmetric carbon atoms. They may therefore exist in the form of enantiomers or of diastereoisomers. These enantiomers and diastereoisomers and also mixtures thereof, including racemic mixtures, are part of the invention.

The compounds of formula (I) may exist in the form of endo/exo stereoisomers. These endo/exo stereoisomers, and also mixtures thereof, are part of the invention.

The compounds of formula (I) may exist in the form of bases or in a form salified with acids or bases, in particular pharmaceutically acceptable acids or bases. Such addition salts are part of the invention.

These salts are advantageously prepared with pharmaceutically acceptable acids, but the salts of other acids that are of use, for example, for purifying or isolating the compounds of formula (I), are also part of the invention.

The compounds of formula (I) may also exist in the form of hydrates or of solvates, i.e. in the form of associations or combinations with one or more water molecules or with a solvent. Such hydrates and solvates are also part of the invention.

In the context of the present invention, and unless otherwise mentioned in the text:
the term "halogen atom" is intended to mean: a fluorine, a chlorine, a bromine or an iodine;
the term "a ($C_1$-$C_5$)alkyl group" is intended to mean: a linear or branched, saturated aliphatic group containing 1 to 5 successive carbon atoms. By way of examples, mention may be made of methyl, ethyl, propyl, isopropyl, butyl, isobutyl, tert-butyl, pentyl, etc. groups;

the term "a (C$_3$-C$_6$)cycloalkyl group" is intended to mean: a cyclic alkyl group containing 3 to 6 carbon atoms. By way of examples, mention may be made of cyclopropyl, methylcyclopropyl, cyclobutyl, cyclopentyl, cyclohexyl, etc. groups;

the term "a (C$_1$-C$_5$)alkoxy group" is intended to mean: an —O—(C$_1$-C$_5$)alkyl radical where the (C$_1$-C$_5$)alkyl group is as defined above;

the term "an aryl group" is intended to mean: a monocyclic or bicyclic aromatic group containing from 5 to 10 carbon atoms. By way of examples of aryl groups, mention may be made of the phenyl group, the thiophene group, the furan group or the naphthalene group;

the term "a heteroaryl group" is intended to mean: a monocyclic or bicyclic aromatic group containing from 5 to 9 carbon atoms and comprising between 1 and 3 heteroatoms, such as nitrogen, oxygen or sulfur. By way of examples of heteroaryl groups, mention may be made of the groups:
pyridine
pyrazine
pyrimidine
pyrazole
oxadiazole
thiazole
imidazole
benzothiophene
quinoline
indole;

the term "a (C$_1$-C$_5$)haloalkyl group" is intended to mean: a (C$_1$-C$_5$)alkyl group as defined above, substituted with 1 to 5 halogen atoms. Mention will, for example, be made of fluoromethyl, difluoromethyl, trifluoromethyl, trichloromethyl or pentafluoroethyl groups;

the term "a heterocycle" is intended to mean: an optionally fused or bridged monocyclic or bicyclic group comprising from 4 to 10 atoms, at least one of which is chosen from oxygen, nitrogen or sulfur atoms. Mention will, for example, be made of 2,3-dihydrobenzofuran and 1,4-benzodioxane groups;

the term "an optionally substituted phenyl group", "an optionally substituted benzyl group" or "an optionally substituted heterocycle" is intended to mean: a phenyl group or a benzyl group or a heterocycle which is optionally substituted with one or more of the groups hereinafter: halogen atoms, the groups: (C$_1$-C$_5$)alkyl; (C$_1$-C$_5$)alkoxy; (C$_1$-C$_5$)haloalkyl, hydroxyl; hydroxy (C$_1$-C$_5$)alkyl, (C$_1$-C$_5$)alkoxy (C$_1$-C$_5$)alkyl; cyano; phenyl; benzyl; —COOR$_5$; —NR$_6$R$_7$; a —COOR$_5$—(C$_1$-C$_5$)alkyl group, an —NR$_6$R$_7$—(C$_1$-C$_5$)alkyl group, a —CONR$_6$R$_7$ group, a —CONR$_6$R$_7$—(C$_1$-C$_5$)alkyl group or an —SO$_2$NR$_6$R$_7$ group.

R$_{1a,b,c,d}$ denotes the groups R$_{1a}$, R$_{1b}$, R$_{1c}$, and R$_{1d}$, and R$_{2a,b}$ denotes the groups R$_{2a}$ and R$_{2b}$.

Among the compounds of formula (I) which are subjects of the invention, mention may be made of a subgroup of particularly preferred compounds in which X is carbon or oxygen, R$_1$ to R$_7$, X, p, r and the dashed-line bond being as defined above.

Among the latter compounds, particularly preferred compounds of the invention are compounds of formula (I) in which:
p and r represent 1;
the dashed-line bond represents a single or double bond;
R$_{1a,b,c,d}$ represent hydrogen, or one of the groups R$_{1a,b,c,d}$ is a halogen and the others are hydrogen;
R$_{2a,b}$ represent hydrogen, or one of the groups R$_{2a,b}$ is a (C$_1$-C$_5$)alkyl group, preferably methyl, and the other group R$_{2a,b}$ is hydrogen;
R$_3$ represents hydrogen;
R$_4$ in position 4 is chosen from the following aryls or heteroaryls:
pyridine
phenyl
pyrazole.

Another group of particularly preferred compounds for the purpose of the invention corresponds to the derivatives of formula (I) in which X represents the carbon atom and the dashed-line bond represents a double bond, and R$_4$ is a phenyl or a pyridine, R$_{1a,b,c,d}$, R$_{2a,b}$, R$_3$, R$_5$ to R$_7$, p and r being as defined above.

Another group of particularly preferred compounds for the purpose of the invention corresponds to the derivatives of formula (I) in which X represents the oxygen atom and the dashed-line bond represents a single bond, and R$_4$ is a phenyl or a pyridine, R$_{1a,b,c,d}$, R$_{2a,b}$, R$_3$, R$_5$ to R$_7$, p and r being as defined above.

Another group of particularly preferred compounds for the purpose of the invention corresponds to the derivatives of formula (I) in which X represents the carbon atom and the dashed-line bond represents a single bond, and R$_4$ is a phenyl, a pyridine or a pyrazole, R$_{1a,b,c,d}$, R$_{2a,b}$, R$_3$, R$_5$ to R$_7$, p and r being as defined above.

Among the compounds of formula (I) according to the invention, mention may be made of:
(3,4-dihydro-2H-quinolin-1-yl)-((1S,3S,5R)-3-pyridin-4-yl-8-azabicyclo[3.2.1]oct-8-yl)methanone
(3,4-dihydro-2H-quinolin-1-yl)-(3-pyridin-3-yl-8-azabicyclo[3.2.1]oct-2-en-8-yl)methanone
(3,4-dihydro-2H-quinolin-1-yl)-(3-pyridin-4-yl-8-azabicyclo[3.2.1]oct-2-en-8-yl)methanone
(3,4-dihydro-2H-quinolin-1-yl)-((1S,5R)-3-pyridin-3-yl-8-azabicyclo[3.2.1]oct-8-yl)methanone
(3,4-dihydro-2H-quinolin-1-yl)-(3-pyridin-2-yl-8-azabicyclo[3.2.1]oct-8-yl)methanone
(3,4-dihydro-2H-quinolin-1-yl)-(3-pyridin-2-yl-8-azabicyclo[3.2.1]oct-8-yl)methanone
(3,4-dihydro-2H-quinolin-1-yl)-(3-phenyl-8-azabicyclo[3.2.1]oct-8-yl)methanone
(3,4-dihydro-2H-quinolin-1-yl)-[3-(6-fluoropyridin-3-yl)-8-azabicyclo[3.2.1]oct-8-yl]methanone
[3-(4-chlorophenyl)-8-azabicyclo[3.2.1]oct-2-en-8-yl]-(3,4-dihydro-2H-quinolin-1-yl)methanone
(3,4-dihydro-2H-quinolin-1-yl)-[3-(2-fluorophenyl)-8-azabicyclo[3.2.1]oct-2-en-8-yl]methanone
(3,4-dihydro-2H-quinolin-1-yl)-[3-(2-ethylphenyl)-8-azabicyclo[3.2.1]oct-2-en-8-yl]methanone
2-[8-(3,4-dihydro-2H-quinoline-1-carbonyl)-8-azabicyclo[3.2.1]oct-2-en-3-yl]benzonitrile
(3,4-dihydro-2H-quinolin-1-yl)-[3-(2-fluoropyridin-3-yl)-8-azabicyclo[3.2.1]oct-2-en-8-yl]methanone
[3-(2-chlorophenyl)-8-azabicyclo[3.2.1]oct-2-en-8-yl]-(3,4-dihydro-2H-quinolin-1-yl)methanone
(3,4-dihydro-2H-quinolin-1-yl)-[3-(2-trifluoromethylphenyl)-8-azabicyclo[3.2.1]oct-2-en-8-yl]methanone
5-[8-(3,4-dihydro-2H-quinoline-1-carbonyl)-8-azabicyclo[3.2.1]oct-2-ene-3-yl]thiophene-2-carbonitrile
(3-benzo[b]thiophen-2-yl-8-azabicyclo[3.2.1]oct-2-en-8-yl)-(3,4-dihydro-2H-quinolin-1-yl)methanone
(3,4-dihydro-2H-quinolin-1-yl)-(3-m-tolyl-8-azabicyclo[3.2.1]oct-2-en-8-yl)methanone
(3,4-dihydro-2H-quinolin-1-yl)-[3-(4-isopropylphenyl)-8-azabicyclo[3.2.1]oct-2-en-8-yl]methanone 4-[8-(3,4-dihydro-2H-quinoline-1-carbonyl)-8-azabicyclo
[3.2.1]oct-2-ene-3-yl]benzonitrile
(3,4-dihydro-2H-quinolin-1-yl)-[3-(4-methoxyphenyl)-8-
azabicyclo[3.2.1]oct-2-en-8-yl]methanone
3-[8-(3,4-dihydro-2H-quinoline-1-carbonyl)-8-azabicyclo
[3.2.1]oct-2-en-3-yl]benzonitrile
(3,4-dihydro-2H-quinolin-1-yl)-[3-(2-methoxyphenyl)-8-
azabicyclo[3.2.1]oct-2-en-8-yl]methanone
2-[8-(3,4-dihydro-2H-quinoline-1-carbonyl)-8-azabicyclo
[3.2.1]oct-2-en-3-yl]benzamide
[3-(2-chlorothiophen-3-yl)-8-azabicyclo[3.2.1]oct-2-en-8-
yl]-(3,4-dihydro-2H-quinolin-1-yl)methanone
(3,4-dihydro-2H-quinolin-1-yl)-[3-(4-ethylphenyl)-8-azabi-
cyclo[3.2.1]oct-2-en-8-yl]methanone
[3-(2,3-dihydrobenzo[1,4]dioxin-6-yl)-8-azabicyclo[3.2.1]
oct-2-en-8-yl]-(3,4-dihydro-2H-quinolin-1-yl)methanone
(3,4-dihydro-2H-quinolin-1-yl)-[3-(1H-indol-4-yl)-8-azabi-
cyclo[3.2.1]oct-2-en-8-yl]methanone
(3,4-dihydro-2H-quinolin-1-yl)-(3-quinolin-5-yl-8-azabicy-
clo[3.2.1]oct-2-en-8-yl)methanone
(3,4-dihydro-2H-quinolin-1-yl)-[3-(6-methoxypyridin-3-
yl)-8-azabicyclo[3.2.1]oct-2-en-8-yl]methanone
(3,4-dihydro-2H-quinolin-1-yl)-[3-(6-methoxypyridin-3-
yl)-8-azabicyclo[3.2.1]oct-2-en-8-yl]methanone
(3,4-dihydro-2H-quinolin-1-yl)-[3-(3-fluorophenyl)-8-
azabicyclo[3.2.1]oct-2-en-8-yl]methanone
[3-(2,3-dihydrobenzofuran-5-yl)-8-azabicyclo[3.2.1]oct-2-
en-8-yl]-(3,4-dihydro-2H-quinolin-1-yl)methanone
(3,4-dihydro-2H-quinolin-1-yl)-[3-(4-trifluoromethylphe-
nyl)-8-azabicyclo[3.2.1]oct-2-en-8-yl]methanone
(3,4-dihydro-2H-quinolin-1-yl)-[3-(4-fluorophenyl)-8-
azabicyclo[3.2.1]oct-2-en-8-yl]methanone
(3,4-dihydro-2H-quinolin-1-yl)-(3-p-tolyl-8-azabicyclo
[3.2.1]oct-2-en-8-yl)methanone
(3,4-dihydro-2H-quinolin-1-yl)-[3-(4-hydroxymethylphe-
nyl)-8-azabicyclo[3.2.1]oct-2-en-8-yl]methanone
N-{4-[8-(3,4-dihydro-2H-quinoline-1-carbonyl)-8-azabicy-
clo[3.2.1]oct-2-ene-3-yl]phenyl}acetamide
4-[8-(3,4-dihydro-2H-quinoline-1-carbonyl)-8-azabicyclo
[3.2.1]oct-2-ene-3-yl]-N,N-dimethylbenzamide
(3,4-dihydro-2H-quinolin-1-yl)-[3-(1H-indol-6-yl)-8-azabi-
cyclo[3.2.1]oct-2-en-8-yl]methanone
(3,4-dihydro-2H-quinolin-1-yl)-[3-(2-methoxypyridin-3-
yl)-8-azabicyclo[3.2.1]oct-2-en-8-yl]methanone
(3,4-dihydro-2H-quinolin-1-yl)-(3-isoquinolin-4-yl-8-
azabicyclo[3.2.1]oct-2-en-8-yl)methanone
[3-(2-chloropyridin-4-yl)-8-azabicyclo[3.2.1]oct-2-en-8-
yl]-(3,4-dihydro-2H-quinolin-1-yl)methanone
(3,4-dihydro-2H-quinolin-1-yl)-(3-naphthalen-1-yl-8-azabi-
cyclo[3.2.1]oct-2-en-8-yl)methanone
(3,4-dihydro-2H-quinolin-1-yl)-(3-thiophen-3-yl-8-azabicy-
clo[3.2.1]oct-2-en-8-yl)methanone
[3-(4-aminophenyl)-8-azabicyclo[3.2.1]oct-2-en-8-yl]-(3,4-
dihydro-2H-quinolin-1-yl)methanone
(3,4-dihydro-2H-quinolin-1-yl)-[3-(6-fluoropyridin-3-yl)-8-
azabicyclo[3.2.1]oct-2-en-8-yl]methanone
(3,4-dihydro-2H-quinolin-1-yl)-[3-(6-fluoro-2-methylpyri-
din-3-yl)-8-azabicyclo[3.2.1]oct-2-en-8-yl]methanone
[3-(2-chloro-6-methylpyridin-3-yl)-8-azabicyclo[3.2.1]-oct-
2-en-8-yl-(3,4-dihydro-2H-quinolin-1-yl)methanone
(3,4-dihydro-2H-quinolin-1-yl)-[3-(2,6-dimethoxypyridin-
3-yl)-8-azabicyclo[3.2.1]oct-2-en-8-yl]methanone
(3,4-dihydro-2H-quinolin-1-yl)-(3-isoquinolin-5-yl-8-
azabicyclo[3.2.1]oct-2-en-8-yl)methanone
(3,4-dihydro-2H-quinolin-1-yl)-[3-(8-methylquinolin-5-yl)-
8-azabicyclo[3.2.1]oct-2-en-8-yl]methanone
(3,4-dihydro-2H-quinolin-1-yl)-[3-(6-ethoxypyridin-3-yl)-
8-azabicyclo[3.2.1]oct-2-en-8-yl]methanone
(3,4-dihydro-2H-quinolin-1-yl)-[3-(2-ethoxypyridin-3-yl)-
8-azabicyclo[3.2.1]oct-2-en-8-yl]methanone
[3-(2,6-difluoropyridin-3-yl)-8-azabicyclo[3.2.1]oct-2-en-
8-yl]-(3,4-dihydro-2H-quinolin-1-yl)methanone
[3-(5-chloro-2-methoxypyridin-4-yl)-8-azabicyclo[3.2.1]
oct-2-en-8-yl]-(3,4-dihydro-2H-quinolin-1-yl)methanone
[3-(2,5-dichloropyridin-3-yl)-8-azabicyclo[3.2.1]oct-2-en-
8-yl]-(3,4-dihydro-2H-quinolin-1-yl)methanone
(3-benzo[b]thiophen-5-yl-8-azabicyclo[3.2.1]oct-2-en-8-
yl)-(3,4-dihydro-2H-quinolin-1-yl)methanone
(3-benzo[b]thiophen-7-yl-8-azabicyclo[3.2.1]oct-2-en-8-
yl)-(3,4-dihydro-2H-quinolin-1-yl)methanone
(3,4-dihydro-2H-quinolin-1-yl)-[3-(1-methyl-1H-indol-2-
yl)-8-azabicyclo[3.2.1]oct-2-en-8-yl]methanone
[3-(6-chloro-4-methylpyridin-3-yl)-8-azabicyclo[3.2.1]oct-
2-en-8-yl]-(3,4-dihydro-2H-quinolin-1-yl)methanone
(3,4-dihydro-2H-quinolin-1-yl)-(3-pyridin-3-yl-8-azabicy-
clo[3.2.1]oct-2-en-8-yl)methanone
(3,4-dihydro-2H-quinolin-1-yl)-(3-pyridin-4-yl-8-azabicy-
clo[3.2.1]oct-2-en-8-yl)methanone
(3,4-dihydro-2H-quinolin-1-yl)-[3-(2H-pyrazol-3-yl)-8-
azabicyclo[3.2.1]oct-2-yl]methanone
(3,4-dihydro-2H-quinolin-1-yl)-[3-(2H-pyrazol-3-yl)-8-
azabicyclo[3.2.1]oct-8-yl]methanone.

In the following, the term "protective group" (Pg) is intended to mean a group which makes it possible, on the one hand, to protect a reactive function such as a hydroxyl or an amine during a synthesis, and on the other hand, to regenerate the intact reactive function at the end of synthesis. Examples of protective groups and also of the methods of protection and deprotection are given in "Protective Groups in Organic Synthesis", Green et al., 3rd edition (John Wiley & Sons, Inc., New York).

In the following, the term "leaving group" (Lg), is intended to mean a group that can be readily cleaved from a molecule by breaking a heterolytic bond with the departure of a pair of electrons. This group thus can be readily replaced with another group in a substitution reaction, for example. Such leaving groups are, for example, halogens or an activated hydroxyl group such as a mesyl, tosyl, triflate, acetyl, para-nitrophenyl, etc. Examples of leaving groups and references for the preparation thereof are given in "Advances in Organic Chemistry", J. March, 3rd edition, Wiley Interscience, p. 310-316.

In accordance with the invention, the compounds of general formula (I) may be prepared according to the processes hereinafter. In the case where X represents a nitrogen atom, it should be substituted either with a group $R_{2a,b}$ (other than H) or with a protective group Pg as defined above.

Scheme 1 (Method 1):

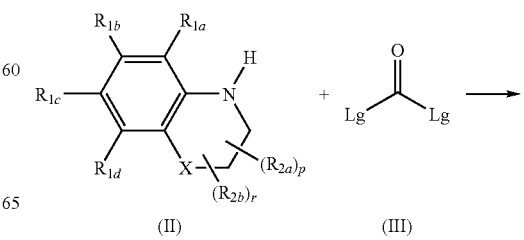

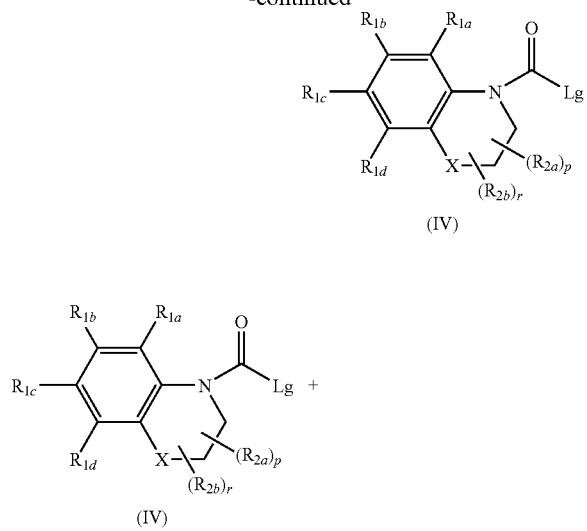

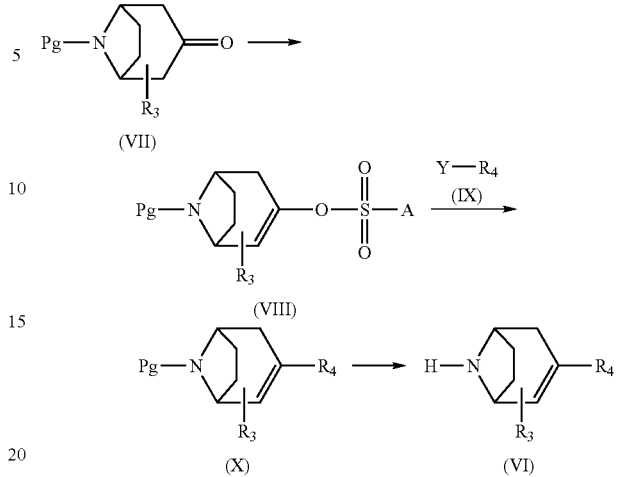

In scheme 1, the compounds of formula (IV) can be prepared by reaction between the intermediates of formula (II) and a carbonyl of formula (III) having two leaving groups Lg (for example, a chlorine atom, a trichloromethoxy group, a para-nitrophenyl group, an imidazole group or a methylimidazolium group) in the presence of a base such as triethylamine or diisopropylamine, in a solvent such as dichloromethane or tetrahydrofuran, at a temperature ranging between ambient temperature and 80° C. The compounds of formulae (I) are obtained by coupling between the activated derivatives (IV) and the amines (V) in the presence or absence of a base such as triethylamine or potassium carbonate, in a solvent such as tetrahydrofuran, dichloromethane, acetonitrile or water, at a temperature ranging from ambient temperature to 100° C.

The heterocycles of general formula (II) are commercially available or can be prepared by methods described in the literature ("Comprehensive heterocyclic chemistry", Katritzky et al., 2nd edition (Pergamon Press)).

The heterocycles of general formula (V) are commercially available or can be prepared by methods described in the literature (Sikazwe et al., Biorg. Med. Chem. Lett 14, 5739 (2004); Gilbert et al., Biorg. Med. Chem. Lett 14, 515 (2004); Lu et al., Biorg. Med. Chem. Lett 13, 1817 (2003)).

Scheme 2 gives details of a synthesis of the compounds of formula (VI) in which the dashed-line bond is a double bond and $R_4$ represents an aryl or heteroaryl group as defined above.

In scheme 2, the heterocycles (VIII), the amine function of which is protected with a protective group Pg (for example, a Boc or Fmoc group), which have a vinyl sulfonate-A group (for example A may be a trifluoromethyl group or a nonafluorobutyl group), can be prepared by conversion of the ketones (VII) with a sulfonating agent such as trifluorosulfonic anhydride or N-phenyltrifluoromethanesulfonimide in the presence of a base such as lithium diisopropylamide or lithium hexamethyl disilazane, in a solvent such as tetrahydrofuran or ethylene glycol dimethyl ether, at a temperature ranging from −78° C. to ambient temperature. The heterocycles (X) are obtained by organometallic coupling between a compound (VIII) and a compound (IX) where Y is a derivative of boron (for example, a boronic acid or a boronic ester) or of tin (for example, a tri(n-butyl)tin) or a halogen atom (for example, bromine or iodine), in the presence of a suitable metal derivative (for example, palladium, zinc or copper derivatives) in the presence or absence of a base, such as potassium carbonate, potassium fluoride or sodium phosphate, in a solvent or mixture of solvents, such as dioxane, ethylene glycol dimethyl ether, toluene or water, at a temperature ranging from ambient temperature to 120° C. In a final step, the amines of formula (VI) are obtained by deprotection of the amine function of the compounds of formula (X), by means of methods chosen from those known to those skilled in the art. They comprise, inter alia, the use of trifluoroacetic acid or of hydrochloric acid in dichloromethane, dioxane, tetrahydrofuran or diethyl ether in the case of a protection with a Boc group, and of piperidine for an Fmoc group, at temperatures ranging from −10 to 100° C.

Scheme 3 gives details of a synthesis of the compounds of formula (XI) in which the dashed-line bond is a single bond and $R_4$ represents an aryl or heteroaryl group as defined above.

Scheme 3:

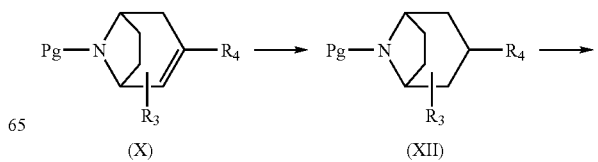

-continued

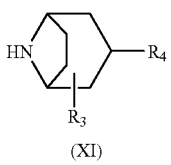
(XI)

In scheme 3, the heterocycles (XII) are obtained by hydrogenation of the double bond of the heterocycles (X) with a suitable metal catalyst in methanol or ethanol. In the second stage, the amines of formula (XI) are obtained by deprotection of the amine function of the compounds of formula (XII) by means of methods chosen from those known to those skilled in the art. They comprise, inter alia, the use of trifluoroacetic acid or of hydrochloric acid in dichloromethane, dioxane, tetrahydrofuran or diethyl ether in the case of a protection with a Boc group, and of piperidine for an Fmoc group, at temperatures ranging from −10 to 100° C.

Optionally, in scheme 4, the mixture of endo(XIII)/exo (XIV) stereoisomers can be separated by means of flash chromatography, of high pressure liquid chromatography or of recrystallization, otherwise it is used as it is and referred to as mixture (XI).

Scheme 4

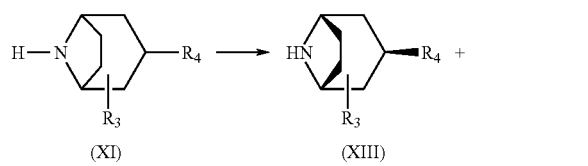

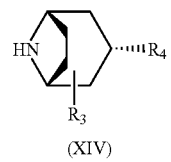
(XIV)

Scheme 5 shows an alternative pathway for preparing the compounds of formula (I) in which the dashed-line bond is a single bond and $R_4$ represents an aryl or heteroaryl group as defined above; these compounds are hereinafter known as compounds of formula (XV). In the case where X represents a nitrogen atom, it should be substituted either with a group $R_{2a,b}$ (other than H), or with a protective group Pg as defined above.

Scheme 5 (Method 2):

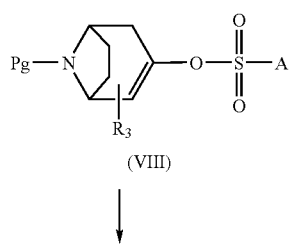

-continued

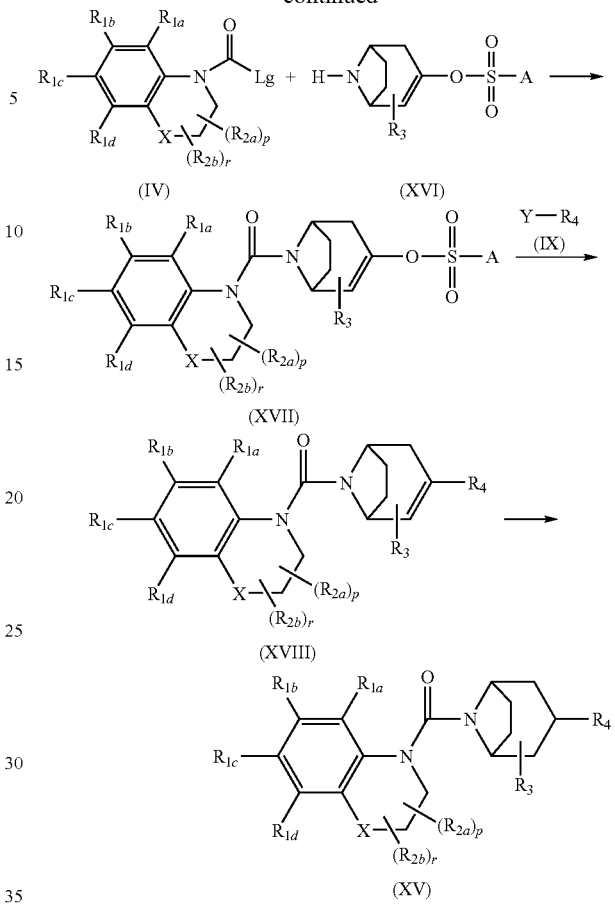

In scheme 5, the amines (XVI) are obtained by deprotection of the amine function of the compounds of formula (VIII), by means of methods chosen from those known to those skilled in the art. They comprise, inter alia, the use of trifluoroacetic acid or of hydrochloric acid in dichloromethane, dioxane, tetrahydrofuran or diethyl ether in the case of a protection with a Boc group, and of piperidine for an Fmoc group, at temperatures ranging from −10 to 100° C. The compounds of formula (XVII) are obtained by coupling between the active derivatives (IV) and the amines (XVI) in the presence or absence of a base such as triethylamine or potassium carbonate, in a solvent such as tetrahydrofuran, dichloromethane, acetonitrile or water, at a temperature ranging from ambient temperature to 100° C. In the following stage, the heterocycles (XVIII) are obtained by organometallic coupling between a compound (XVII) and a compound (IX) where Y is a derivative of boron (for example, a boronic acid or a boronic ester), or of tin (for example, a tri(n-butyl)tin group) or a halogen atom (for example bromine or iodine), in the presence of a suitable metal derivative (for example, a palladium, zinc or copper derivative) in the presence or absence of a base, such as potassium carbonate, potassium fluoride or sodium phosphate, in a solvent or mixture of solvents, such as dioxane, ethylene glycol dimethyl ether, toluene or water, at a temperature ranging from ambient temperature to 120° C. In a final step, the double bond of the heterocycles (XVIII) is hydrogenated with a suitable metal in methanol or ethanol, so as to give the derivatives (XV).

Optionally, in scheme 6, the mixture of endo(XIX)/exo (XX) stereoisomers can be separated by means of flash chromatography, of high pressure liquid chromatography or of recrystallization, otherwise it is used as it is and referred to as mixture (XV).

Scheme 6:

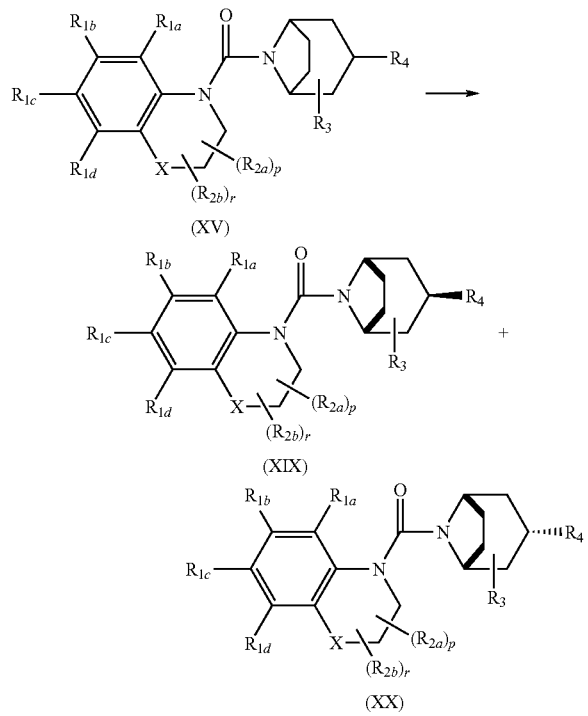

EXAMPLES

The following examples describe the preparation of certain compounds in accordance with the invention. These examples are not limiting and merely illustrate the present invention. The numbers of the compounds exemplified refer back to those given in the table hereinafter which illustrates the chemical structures and physical properties of some compounds according to the invention.

Example 1

1-[(3-pyridin-3-yl-8-azabicyclo[3.2.1]oct-8-yl)carbonyl]-1,2,3,4-tetrahydroquinoline Hydrochloride (Compound 4)

1.1: tert-butyl 3-{[(trifluoromethyl)sulfonyl]oxy}-8-azabicyclo[3.2.1]oct-2-ene-8-carboxylate 10 ml of a 2.5N solution n-butyl lithium in hexane are added, dropwise to a solution of 3.73 ml of diisopropylamine in 100 ml of tetrahydrofuran cooled to −60° C., in a 500 ml three-necked flask under nitrogen. After stirring for ¼ hour, 5 g of N-tert-butyloxycarbonyl nortropinone in tetrahydrofuran (50 ml) at 0° C. are added. Finally, still at 0° C., 8.32 g of N-phenyltrifluoromethanesulfonimide are added. After stirring for 24 hours at ambient temperature, the tetrahydrofuran is evaporated off and the product is purified by rapid filtration over alumina, using a 2/1 mixture of heptane/ethyl acetate as eluent. 6.13 g of tert-butyl 3-{[(trifluoromethyl)sulfonyl]oxy}-8-azabicyclo[3.2.1]oct-2-ene-8-carboxylate are obtained

M+H$^+$=358.

1.2: 8-azabicyclo[3.2.1]oct-2-ene-3-yl Trifluoromethylsulfonate Hydrochloride 2.76 g of tert-butyl 3-{[(trifluoromethyl)sulfonyl]oxy}-8-azabicyclo[3.2.1]oct-2-ene-8-carboxylate in 13 ml of dioxane are placed in a 100 ml round-bottomed flask. 12.8 ml of a 4N solution of hydrochloric acid in dioxane are then carefully added. The reaction mixture is stirred for 3 h. The dioxane is evaporated off, to give 2.27 g of 8-azabicyclo[3.2.1]oct-2-ene-3-yl trifluoromethylsulfonate hydrochloride.

M+H$^+$=258

1.3: 8-(3,4-dihydroquinolin-1(2H)-ylcarbonyl)-8-azabicyclo[3.2.1]oct-2-ene-3-yl Trifluoromethanesulfonate 1.13 g of 1,2,3,4-tetrahydroquinoline, 85 ml of dichloromethane and 1.54 ml of triethylamine are placed in a 250 ml three-necked flask under a nitrogen atmosphere. 0.834 g of triphosgene is added at 0° C., and the reaction is then left to stir at ambient temperature for 4 h. 2.27 g of 8-azabicyclo[3.2.1]oct-2-ene-3-yl trifluoromethylsulfonate hydrochloride and 1.19 ml of triethylamine are subsequently added and the reaction mixture is then refluxed for 18 h. 200 ml of a saturated aqueous solution of sodium hydrogen carbonate are added and the aqueous phase is extracted three times with dichloromethane. The organic phases are combined, dried over sodium sulfate and evaporated under reduced pressure. The residue is chromatographed on silica gel with an 8/2 mixture of heptane/ethyl acetate. 3.21 g of 8-(3,4-dihydroquinolin-1(2H)-ylcarbonyl)-8-azabicyclo[3.2.1]oct-2-ene-3-yl trifluoromethanesulfonate are obtained.

M+H$^+$=417

1.4: 1-[(3-pyridin-3-yl-8-azabicyclo[3.2.1]oct-2-en-8-yl)carbonyl]-1,2,3,4-tetrahydroquinoline 0.5 g of dihydroquinolin-1(2H)-ylcarbonyl)-8-azabicyclo[3.2.1]oct-2-ene-3-yl trifluoromethanesulfonate, 0.419 g of 3-(4,4,5,5-tetramethyl-1,3,2-dioxaborolan-2-yl)pyridine, 0.1 g of lithium chloride, 0.765 g of potassium phosphate, 0.067 g of 2'-(dimethylamino)-2-biphenylpalladium(II)chloride dinorbornylphosphine and 4.3 ml of dioxane are introduced into a 10 ml glass tube. The tube is sealed, and then heated at 100° C. under microwave radiation for 50 minutes. Water and ethyl acetate are added. The aqueous phase is extracted three times with ethyl acetate. The organic phases are combined, dried over sodium sulfate and the solvent is evaporated off under reduced pressure. The residue is chromatographed on silica gel with a 3/7 mixture of heptane/ethyl acetate. 0.3 g of 1-[(3-pyridin-3-yl-8-azabicyclo[3.2.1]oct-2-en-8-yl)carbonyl]-1,2,3,4-tetrahydroquinoline is obtained.

M+H$^+$=346

1.5: 1-[(3-pyridin-3-yl-8-azabicyclo[3.2.1]oct-8-yl)carbonyl]-1,2,3,4-tetrahydroquinoline In a high-pressure reactor, under nitrogen, 0.148 g of 5% palladium-on-charcoal is added to 0.240 g of 1-[(3-pyridin-3-yl-8-azabicyclo[3.2.1]oct-2-en-8-yl)carbonyl]-1,2,3,4-tetrahydroquinoline solubilized in 9 ml of ethanol. The reaction mixture is placed under a hydrogen pressure of 3 atmospheres, at 25° C., and mechanically stirred for 15 hours. The palladium is filtered off on Whatman paper and washed with methanol. The solvent is evaporated off, and the residue then chromatographed on silica gel with an eluent gradient of heptane/ethyl acetate (3/7) to heptane/ethyl acetate (2/8). 0.146 g of 1-[(3-pyridin-3-yl-8-azabicyclo[3.2.1]oct-8-yl)carbonyl]-1,2,3,4-tetrahydroquinoline is obtained.
M+H$^+$=348.3

1.6: 1-[(3-pyridin-3-yl-8-azabicyclo[3.2.1]oct-8-yl)carbonyl]-1,2,3,4-tetrahydroquinoline Hydrochloride 0.146 g of 1-[(3-pyridin-3-yl-8-azabicyclo[3.2.1]oct-8-yl)carbonyl]-1,2,3,4-tetrahydroquinoline is dissolved in 6 ml of dichloromethane and 4.2 ml of a 4N solution of hydrochloric acid in dioxane are added. After evaporation, the residue is taken up in ethyl acetate. The precipitate is filtered off and then dried under vacuum. 0.122 g of 1-[(3-pyridin-3-yl-8-azabicyclo[3.2.1]oct-8-yl)carbonyl]-1,2,3,4-tetrahydroquinoline hydrochloride is obtained.
Melting point=218-220° C.
M+H$^+$=348.3
$^1$H NMR (DMSO, 200 MHz), δ (ppm): 1.4-2 (m, 9H); 2.2-2.44 (m, 1H); 2.6-2.78 (t, 2H); 2.9-3.1 (m, 0.4H); 3.2-3.45 (m, 0.6H); 3.5-3.61 (m, 2H); 4.1 (sl, 2H); 6.78-6.98 (m, 1H); 7-7.2 (m, 3H); 7.8-7.96 (m, 1H); 8.3-8.55 (m, 1H); 8.64-8.9 (m, 2H)

Example 2

1-{[(3-endo)-3-pyridin-2-yl-8-azabicyclo-[3.2.1]oct-8-yl]carbonyl}-1,2,3,4-tetrahydroquinoline (Compound 5)

2.1 1-[(3-pyridin-2-yl-8-azabicyclo[3.2.1]oct-2-en-8-yl]carbonyl}-1,2,3,4-tetrahydroquinoline 2.87 g of tri(n-butyl)tin 2-pyridine, 0.6 g of lithium chloride, 0.5 g of dihydroquinolin-1(2H)-ylcarbonyl)-8-azabicyclo[3.2.1]oct-2-en-3-yl trifluoromethanesulfonate, 0.249 g of diphenylphosphinepalladium(II)dichloride and 19 ml of tetrahydrofuran are introduced into an 80 ml glass tube. The tube is sealed and then heated at 140° C. under microwave irradiation for 1 hour. The reaction mixture is filtered and then ethyl acetate and a 0.5N aqueous solution of potassium fluoride are added. The mixture is subsequently filtered, the organic phase is then dried over sodium sulfate and the solvent evaporated off under reduced pressure. The residue is chromatographed on silica gel with a mixture of heptane/ethyl acetate. 0.73 g of 1-[(3-pyridin-2-yl-8-azabicyclo[3.2.1]oct-2-en-8-yl)carbonyl]-1,2,3,4-tetrahydroquinoline is obtained.
M+H$^+$=346

2.2 1-{[(3-endo)-3-pyridin-2-yl-8-azabicyclo[3.2.1]-oct-8-yl]carbonyl}-1,2,3,4-tetrahydroquinoline In a high-pressure reactor, under nitrogen, 0.5 g of 5% palladium-on-charcoal is added to 0.81 g of 1-[(3-pyridin-2-yl-8-azabicyclo[3.2.1]oct-2-en-8-yl)carbonyl]-1,2,3,4-tetrahydroquinoline solubilized in 29 ml of ethanol. The reaction mixture is placed under a hydrogen pressure of 3 atmospheres, at 25° C., and mechanically stirred for 7 hours. The palladium is filtered off on Whatman paper and washed with methanol. The solvent is evaporated off and the residue is then chromatographed on silica gel, with a heptane/ethyl acetate eluent gradient. 0.221 g of 1-{[(3-endo)-3-pyridin-2-yl-8-azabicyclo[3.2.1]oct-8-yl]-carbonyl}-1,2,3,4-tetrahydroquinoline and 0.141 g of 1-{[(3-exo)-3-pyridin-2-yl-8-azabicyclo[3.2.1]oct-8-yl]carbonyl}-1,2,3,4-tetrahydroquinoline are obtained.
M+H$^+$=348.3

2.3 1-{[(3-endo)-3-pyridin-2-yl-8-azabicyclo[3.2.1]-oct-8-yl]carbonyl}-1,2,3,4-tetrahydroquinoline hydrochloride 0.221 g of 1-{[(3-endo)-3-pyridin-2-yl-8-azabicyclo-[3.2.1]oct-8-yl]carbonyl}-1,2,3,4-tetrahydroquinoline is dissolved in 5.3 ml of dichloromethane, and 6.4 ml of a 0.2N solution of hydrochloric acid in ether are added. After evaporation, the residue is taken up in ethyl acetate. The precipitate is filtered off and then dried under vacuum. 0.161 g of 1-{[(3-endo)-3-pyridin-2-yl-8-azabicyclo[3.2.1]oct-8-yl]carbonyl}-1,2,3,4-tetrahydroquinoline hydrochloride is obtained.
Melting point=161-163° C.
M+H$^+$=348.3
$^1$H NMR (CDCl$_3$, 200 MHz), δ (ppm): 1.36-1.56 (m, 2H); 1.67-1.8 (m, 2H); 1.85-2.1 (m, 4H); 2.24-2.4 (m, 2H); 2.7 (t, 2H); 3 (q, 1H); 3.62 (t, 2H); 4-4.12 (m, 2H); 6.82 (t, 1H); 6.93-7.09 (m, 3H); 7.15-7.3 (m, 2H); 7.43-7.59 (m, 1H); 8.4-8.5 (m, 1H).

Example 3

1-{[(3-exo)-3-pyridin-2-yl-8-azabicyclo-[3.2.1]oct-8-yl]carbonyl}-1,2,3,4-tetrahydroquinoline Hydrochloride (Compound 6)

0.13 g of 1-{[(3-exo)-3-pyridin-2-yl-8-azabicyclo-[3.2.1]oct-8-yl]carbonyl}-1,2,3,4-tetrahydroquinoline obtained according to example 2 (part 2.2) is dissolved in 3.1 ml of dichloromethane, and 3.7 ml of a 0.2N solution of hydrochloric acid in ether are added. After evaporation, the residue is taken up in ethyl acetate. The precipitate is filtered off and then dried under vacuum. 0.101 g of 1-{[(3-exo)-3-pyridin-2-yl-8-azabicyclo-[3.2.1]oct-8-yl]carbonyl}-1,2,3,4-tetrahydroquinoline hydrochloride is obtained.
Melting point=178-180° C.
M+H$^+$=348.3
$^1$H NMR (CDCl$_3$, 200 MHz), δ (ppm): 1.65-2 (m, 10H); 2.7 (t, 2H); 3.09-3.3 (m, 1H); 3.2 (t, 2H); 4-4.2, (t, 2H); 6.84 (t, 1H); 6.95-7.23 (m, 5H); 7.5-7.67 (m, 1H); 8.45 (d, 1H).

Example 4

1-[(4-pyridin-3-yl-8-azabicyclo[3.2.1]oct-8-yl)carbonyl]-1,2,3,4-tetrahydroquinoline Hydrochloride (Compound 1)

4.1 Tert-Butyl 3-pyridin-4-yl-8-azabicyclo[3.2.1]oct-2-ene-8-carboxylate 1 g of tert-butyl 3-{[(trifluoromethyl)sulfonyl]oxy}-8-azabicyclo[3.2.1]oct-2-ene-8-carboxylate, 0.975 g of 4-(4,4,5,5-tetramethyl-1,3,2-dioxaborolan-2-yl)pyridine, 0.24 g of lithium chloride, 1.78 g of potassium phosphate, 0.157 g of 2'-(dimethylamino)-2-biphenylpalladium(II)chloride dinorbornylphosphine and 10 ml of dioxane are introduced into an 80 ml glass tube. The tube is sealed and then heated at 100° C. under microwave irradiation for 30 minutes. Water and ethyl acetate are added. The aqueous phase is extracted three times with ethyl acetate. The organic phases are combined and dried over sodium sulfate and the solvent is evaporated off under reduced pressure. The residue is chromatographed on silica gel with a mixture of heptane/ethyl acetate. 0.458 g of tert-butyl 3-pyridin-4-yl-8-azabicyclo[3.2.1]oct-2-ene-8-carboxylate is obtained
M+H$^+$=387.

4.2 Tert-Butyl 3-pyridin-4-yl-B-azabicyclo[3.2.1]-octane-8-carboxylate

In a high-pressure reactor, under nitrogen, 0.17 g of 5% palladium-on-charcoal is added to 0.46 g of tert-butyl 3-pyridin-4-yl-8-azabicyclo[3.2.1]oct-2-ene-8-carboxylate solubilized in 20 ml of methanol. The reaction mixture is placed under a hydrogen pressure of 3 atmospheres at 25° C., and mechanically stirred for two and a half hours. The palladium is filtered off on Whatman paper and washed with methanol. The solvent is evaporated off and 0.46 g of tert-butyl 3-pyridin-4-yl-8-azabicyclo[3.2.1]octane-8-carboxylate is obtained.

M+H$^+$=289

4.3 3-pyridin-4-yl-8-azabicyclo[3.2.1]octane Dihydrochloride 2.76 g of tert-butyl 3-pyridin-4-yl-8-azabicyclo[3.2.1]octane-8-carboxylate and 4 ml of a 4N solution of hydrochloric acid in dioxane are placed in a 10 ml round-bottomed flask. The reaction mixture is stirred for one and a half hours. The dioxane is evaporated off and 0.341 g of 3-pyridin-4-yl-8-azabicyclo[3.2.1]octane dihydrochloride is obtained.

M+H$^+$=189

4.4 1-[(4-pyridin-3-yl-8-azabicyclo[3.2.1]oct-8-yl) carbonyl]-1,2,3,4-tetrahydroquinoline 0.241 g of 1,2,3,4-tetrahydroquinoline, 20 ml of dichloromethane and 0.24 ml of triethylamine are placed in a 50 ml round-bottomed flask under a nitrogen atmosphere. 0.178 g of triphosgene is added at 0° C. and then the reaction mixture is left to stir at ambient temperature for 3 h. 0.34 g of 3-pyridin-4-yl-8-azabicyclo[3.2.1]octane dihydrochloride and 1.19 ml of triethylamine are subsequently added and the reaction mixture is then refluxed for three hours. 200 ml of a saturated aqueous solution of sodium hydrogen carbonate are added and the aqueous phase is then extracted three times with dichloromethane. The organic phases are combined, dried over sodium sulfate and evaporated under reduced pressure. The residue is chromatographed on silica gel with a 9/1 mixture of dichloromethane/methanol. 0.04 g of 1-[(4-pyridin-3-yl-8-azabicyclo[3.2.1]oct-8-yl)carbonyl]-1,2,3,4-tetrahydroquinoline is obtained.

M+H$^+$=348

4.5 1-[(4-pyridin-3-yl-8-azabicyclo[3.2.1]oct-8-yl) carbonyl]-1,2,3,4-tetrahydroquinoline Hydrochloride 0.04 g of 1-[(4-pyridin-3-yl-8-azabicyclo[3.2.1]oct-8-yl) carbonyl]-1,2,3,4-tetrahydroquinoline is dissolved in 1.15 ml of a 0.2N solution of hydrochloric acid in ether. After evaporation, the residue is taken up in ethyl acetate. The precipitate is filtered off and then dried under vacuum. 0.004 g of 1-[(4-pyridin-3-yl-8-azabicyclo[3.2.1]oct-8-yl)carbonyl]-1,2,3,4-tetrahydroquinoline hydrochloride is obtained.

Melting point=216-222° C.

M+H$^+$=348.2

$^1$H NMR (DMSO, 200 MHz), δ (ppm): 1.65-1.95 (m, 10H); 2.65 (t, 2H); 3.2-3.4 (m, 1H); 3.45 (t, 2H); 4.05 (sl, 1H); 6.75-6.9 (m, 1H); 6.95-7.2 (m, 2H); 7.78 (d, 2H); 8.64 (d, 2H).

The table which follows illustrates the chemical structures and the physical properties of some examples of compounds according to the invention. In this table:

in the "salt" column "-" represents a compound in the form of a free base, while "HCl" represents a compound in hydrochloride form.

TABLE

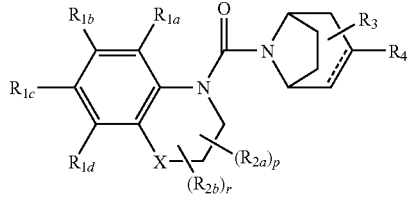

(I)

in examples 1 to 64 below: p = r = 1 and $R_{2a}$ = $R_{2b}$ = H

| No. | X | ---- | $R_{1a}$ | $R_{1b}$ | $R_{1c}$ | $R_{1d}$ | $R_3$ | Endo/exo | $R_4$ | Salt | Mp (° C.) | LCUVMS MASS (amu) | Method |
|---|---|---|---|---|---|---|---|---|---|---|---|---|---|
| 1 | C | — | H | H | H | H | H | Endo/exo | 4-pyridyl | HCl | 211-216 | | 1 |
| 2 | C | = | H | H | H | H | H | — | 3-pyridyl | HCl | 150-176 | | 2 |
| 3 | C | = | H | H | H | H | H | — | 4-pyridyl | HCl | 218-222 | | 2 |

TABLE-continued
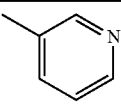
in examples 1 to 64 below: p = r = 1 and $R_{2a} = R_{2b} = H$
| No. | X | ---- | $R_{1a}$ | $R_{1b}$ | $R_{1c}$ | $R_{1d}$ | $R_3$ | Endo/exo | $R_4$ | Salt | Mp (° C.) | LCUVMS MASS (amu) | Method |
|---|---|---|---|---|---|---|---|---|---|---|---|---|---|
| 4 | C | — | H | H | H | H | H | Endo/exo | 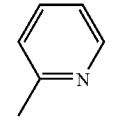 | HCl | 218-222 | | 2 |
| 5 | C | — | H | H | H | H | H | Endo | 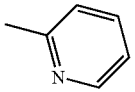 | HCl | 161-163 | | 2 |
| 6 | C | — | H | H | H | H | H | Exo | 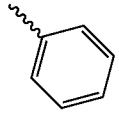 | HCl | 178-180 | | 2 |
| 7 | C | — | H | H | H | H | H | Endo/exo | 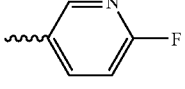 | — | 133-134 | | 2 |
| 8 | C | — | H | H | H | H | H | Endo/exo |  | HCl | 98-99 | | 2 |
| 9 | C | = | H | H | H | H | H | — | 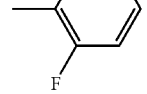 | — | — | 379.22 | 2 |
| 10 | C | = | H | H | H | H | H | — | 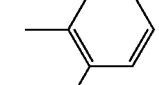 | — | — | 363.24 | 2 |
| 11 | C | = | H | H | H | H | H | — | 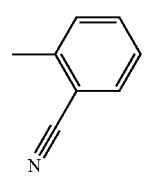 | — | — | 373.32 | 2 |
| 12 | C | = | H | H | H | H | H | — | 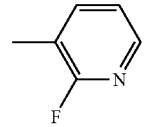 | — | — | 370.24 | 2 |
| 13 | C | — | H | H | H | H | H | — |  | — | — | 364.23 | 2 |

TABLE-continued (I)

in examples 1 to 64 below: p = r = 1 and R$_{2a}$ = R$_{2b}$ = H

| No. | X | ---- | R$_{1a}$ | R$_{1b}$ | R$_{1c}$ | R$_{1d}$ | R$_3$ | Endo/exo | R$_4$ | Salt | Mp (° C.) | LCUVMS MASS (amu) | Method |
|---|---|---|---|---|---|---|---|---|---|---|---|---|---|
| 14 | C | = | H | H | H | H | H | — | 2-chlorophenyl with methylene | — | — | 379.21 | 2 |
| 15 | C | = | H | H | H | H | H | — | 2-(trifluoromethyl)phenyl with methylene | — | — | 413.23 | 2 |
| 16 | C | = | H | H | H | H | H | — | 5-methyl-thiophene-2-carbonitrile | — | — | 376.24 | 2 |
| 17 | C | = | H | H | H | H | H | — | benzothiophene | — | — | 401.28 | 2 |
| 18 | C | = | H | H | H | H | H | — | 3-methylphenyl with methylene | — | — | 359.29 | 2 |
| 19 | C | = | H | H | H | H | H | — | 4-isopropylphenyl with methylene | — | — | 387.34 | 2 |
| 20 | C | = | H | H | H | H | H | — | 4-cyanophenyl with methylene | — | — | 370.27 | 2 |
| 21 | C | = | H | H | H | H | H | — | 4-methoxyphenyl with methylene | — | — | 375.26 | 2 |
| 22 | C | = | H | H | H | H | H | — | 3-cyanophenyl with methylene | — | — | 370.21 | 2 |

TABLE-continued

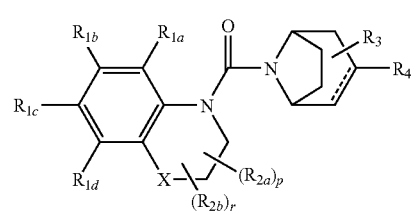

in examples 1 to 64 below: p = r = 1 and $R_{2a} = R_{2b} = H$

| No. | X | ---- | $R_{1a}$ | $R_{1b}$ | $R_{1c}$ | $R_{1d}$ | $R_3$ | Endo/exo | $R_4$ | Salt | Mp (° C.) | LCUVMS MASS (amu) | Method |
|---|---|---|---|---|---|---|---|---|---|---|---|---|---|
| 23 | C | = | H | H | H | H | H | — | 2-methoxyphenyl-methyl | — | — | 375.26 | 2 |
| 24 | C | = | H | H | H | H | H | — | 2-carbamoylphenyl-methyl | — | — | 388.21 | 2 |
| 25 | C | = | H | H | H | H | H | — | 2-chloro-3-methyl-thiophen | — | — | 385.16 | 2 |
| 26 | C | = | H | H | H | H | H | — | 4-ethylphenyl-methyl | — | — | 373.27 | 2 |
| 27 | C | = | H | H | H | H | H | — | 2,3-dihydrobenzodioxin-methyl | — | — | 403.23 | 2 |
| 28 | C | = | H | H | H | H | H | — | 1H-indol-4-yl-methyl | — | — | 384.23 | 2 |
| 29 | C | = | H | H | H | H | H | — | quinolin-5-yl-methyl | TFA | — | 396.25 | 2 |
| 30 | C | = | H | H | H | H | H | — | 1-methyl-1H-indol-5-yl-methyl | TFA | — | 398.24 | 2 |

TABLE-continued
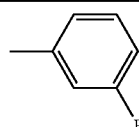
(I)
in examples 1 to 64 below: p = r = 1 and $R_{2a} = R_{2b} = H$
| No. | X | ---- | $R_{1a}$ | $R_{1b}$ | $R_{1c}$ | $R_{1d}$ | $R_3$ | Endo/exo | $R_4$ | Salt | Mp (° C.) | LCUVMS MASS (amu) | Method |
|---|---|---|---|---|---|---|---|---|---|---|---|---|---|
| 31 | C | = | H | H | H | H | H | — | 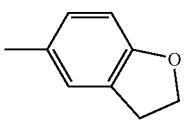 | — | — | 363.17 | 2 |
| 32 | C | = | H | H | H | H | H | — | 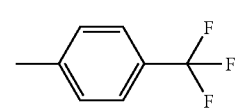 | — | — | 387.22 | 2 |
| 33 | C | = | H | H | H | H | H | — |  | — | — | 413.19 | 2 |
| 34 | C | = | H | H | H | H | H | — | 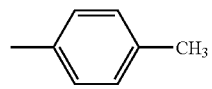 | — | — | 363.17 | 2 |
| 35 | C | = | H | H | H | H | H | — | 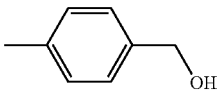 | — | — | 359.18 | 2 |
| 36 | C | = | H | H | H | H | H | — | 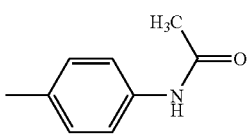 | — | — | 375.26 | 2 |
| 37 | C | = | H | H | H | H | H | — | 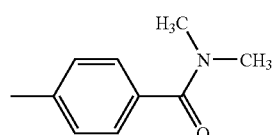 | — | — | 402.3 | 2 |
| 38 | C | = | H | H | H | H | H | — | 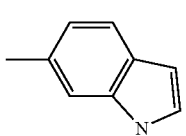 | — | — | 416.26 | 2 |
| 39 | C | = | H | H | H | H | H | — | 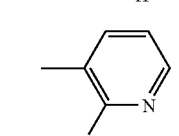 | TFA | — | 384.23 | 2 |
| 40 | C | = | H | H | H | H | H | — |  | TFA | — | 376.19 | 2 |

TABLE-continued

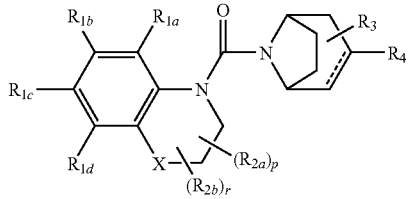

(I)

in examples 1 to 64 below: p = r = 1 and $R_{2a} = R_{2b}$ = H

| No. | X | ---- | $R_{1a}$ | $R_{1b}$ | $R_{1c}$ | $R_{1d}$ | $R_3$ | Endo/exo | $R_4$ | Salt | Mp (° C.) | LCUVMS MASS (amu) | Method |
|---|---|---|---|---|---|---|---|---|---|---|---|---|---|
| 41 | C | = | H | H | H | H | H | — | 5-isoquinolinyl | TFA | — | 396.23 | 2 |
| 42 | C | = | H | H | H | H | H | — | 2-chloro-4-pyridinyl | — | — | 380.5 | 2 |
| 43 | C | = | H | H | H | H | H | — | 1-naphthyl | — | — | 395.25 | 2 |
| 44 | C | = | H | H | H | H | H | — | 3-thienyl | — | — | 351.15 | 2 |
| 45 | C | = | H | H | H | H | H | — | 4-aminophenyl | TFA | — | 360.26 | 2 |
| 46 | C | = | H | H | H | H | H | — | 6-fluoro-3-pyridinyl | — | — | 364.18 | 2 |
| 47 | C | = | H | H | H | H | H | — | 6-fluoro-2-methyl-3-pyridinyl | — | — | 378.21 | 2 |
| 48 | C | = | H | H | H | H | H | — | 2-chloro-6-methyl-3-pyridinyl | — | — | 394.18 | 2 |
| 49 | C | = | H | H | H | H | H | — | 2,6-dimethoxy-3-pyridinyl | — | — | 406.17 | 2 |

TABLE-continued (I)

in examples 1 to 64 below: p = r = 1 and $R_{2a} = R_{2b} = H$

| No. | X | ---- | $R_{1a}$ | $R_{1b}$ | $R_{1c}$ | $R_{1d}$ | $R_3$ | Endo/exo | $R_4$ | Salt | Mp (°C.) | LCUVMS MASS (amu) | Method |
|---|---|---|---|---|---|---|---|---|---|---|---|---|---|
| 50 | C | = | H | H | H | H | H | — | isoquinolinyl | TFA | — | 396.22 | 2 |
| 51 | C | = | H | H | H | H | H | — | 5,8-dimethylquinolinyl | TFA | — | 410.2 | 2 |
| 52 | C | = | H | H | H | H | H | — | 2-ethoxy-5-methylpyridinyl | TFA | — | 390.2 | 2 |
| 53 | C | = | H | H | H | H | H | — | 2-ethoxy-3-methylpyridinyl | TFA | — | 390.17 | 2 |
| 54 | C | = | H | H | H | H | H | — | 2,6-difluoro-3-methylpyridinyl | — | — | 382.19 | 2 |
| 55 | C | = | H | H | H | H | H | — | 2-chloro-5-methoxy-3-methylpyridinyl | — | — | 410.18 | 2 |
| 56 | C | = | H | H | H | H | H | — | 2,5-dichloro-3-methylpyridinyl | — | — | 414.13 | 2 |
| 57 | C | = | H | H | H | H | H | — | methylbenzothiophenyl | — | — | 401.18 | 2 |

TABLE-continued (I)

in examples 1 to 64 below: p = r = 1 and $R_{2a} = R_{2b} = H$

| No. | X | ---- | $R_{1a}$ | $R_{1b}$ | $R_{1c}$ | $R_{1d}$ | $R_3$ | Endo/exo | $R_4$ | Salt | Mp (°C.) | LCUVMS MASS (amu) | Method |
|---|---|---|---|---|---|---|---|---|---|---|---|---|---|
| 58 | C | = | H | H | H | H | H | — | benzothiophene-methyl | — | — | 401.17 | 2 |
| 59 | C | = | H | H | H | H | H | — | 1-methyl-2-methylindole | — | — | 398.24 | 2 |
| 60 | C | = | H | H | H | H | H | — | 2-chloro-4-methyl-pyridine-methyl | — | — | 394.16 | 2 |
| 61 | C | = | H | H | H | H | H | — | 3-methylpyridine | — | — | 346 | 2 |
| 62 | C | = | H | H | H | H | H | — | 4-methylpyridine | — | — | 346.2 | 2 |
| 63 | C | — | H | H | H | H | H | endo | pyrazole-methyl | — | 146-166 | | 2 |
| 64 | C | — | H | H | H | H | H | exo | pyrazole-methyl | — | 70-81 | | 2 |

The compounds according to the invention were the subject of pharmacological tests for determining their inhibitory activity on the 11beta-HSD1 enzyme which is an enzyme involved in lipid metabolism or glucose metabolism.

These tests consisted in measuring the in vitro inhibitory activity of the compounds of the invention by virtue of an SPA (Scintillation Proximity Assay) in 384 well format. The recombinant 11beta-HSD1 protein was produced in the yeast *S. cerevisiae*. The reaction was carried out by incubating the enzyme in the presence of $^3$H-cortisone and NADPH, in the absence or in the presence of an increasing concentration of inhibitor. SPA beads coupled to an anti-mouse antibody, preincubated with an anti-cortisol antibody, made it possible to - measure the amount of cortisol formed during the course of the reaction.

The inhibitory activity with respect to the 11beta-HSD1 enzyme is given by the concentration which inhibits 50% of the activity of 11beta-HSD1 ($IC_{50}$).

The $IC_{50}$ values of the compounds according to the invention are less than 1 µM. For example, the $IC_{50}$ values of compounds No. 4, 7, 13, 28 and 55 are, respectively, 0.019 µM, 0.004 µM, 0.122 µM, 0.19 µM and 0.534 µM.

It therefore appears that the compositions according to the invention have an inhibitory activity on the 11beta-HSD1 enzyme. The compounds according to the invention can therefore be used for the preparation of medicaments, in particular for medicaments that inhibit the 11beta-HSD1 enzyme.

Thus, according to another of its aspects, a subject of the invention is medicaments which comprise a compound of formula (I), or an addition salt of the latter with a pharmaceutically acceptable acid, or else a hydrate or a solvate of the compound of formula (I).

These medicaments are of use in therapy, in particular in the treatment of obesity, diabetes, insulin resistance, metabolic syndrome, Cushing's syndrome, hypertension, atherosclerosis, cognition and dementia, glaucoma, osteoporosis and certain infectious diseases by increasing the efficacy of the immune system.

According to another of its aspects, the present invention relates to pharmaceutical compositions comprising a compound according to the invention as active ingredient. These pharmaceutical compositions contain an effective dose of at least one compound according to the invention or a pharmaceutically acceptable salt, a hydrate or a solvate of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or the optional salt, solvate or hydrate thereof, may be administered in unit administration form, as a mixture with conventional pharmaceutical excipients, to animals and to human beings for the prophylaxis or treatment of the conditions or diseases above.

Suitable unit administration forms comprise oral administration forms such as tablets, soft or hard gel capsules, powders, granules and oral solutions or suspensions, sublingual, buccal, intratracheal, intraocular, or intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathologies indicated above, which comprises administering an effective dose of a compound according to the invention or a pharmaceutically acceptable salt or hydrate or solvate thereof, to a patient.

We claim:

1. A compound of formula (I)

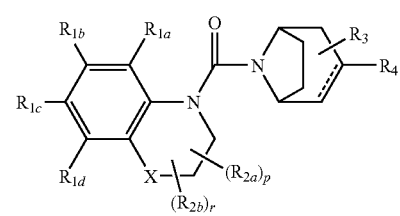

wherein:

X is a carbon;

---- is a single bond or a double bond;

$R_{1a}$, $R_{1b}$, $R_{1c}$, $R_{1d}$, $R_{2a}$ and $R_{2b}$ are hydrogen, $R_3$ is hydrogen;

$R_4$ is:

hydrogen or $(C_1-C_5)$alkyl, $(C_3-C_6)$cycloalkyl, heterocyclyl, $(C_5-C_{10})$ monocyclic or bicyclic aryl, or $(C_2-C_9)$ monocyclic or bicyclic heteroaryl, wherein the aryl or heteroaryl group is optionally substituted with 1 to 4 substituents chosen from the group consisting of halogen, $(C_1-C_5)$alkyl, $(C_1-C_5)$alkoxy, $(C_1-C_5)$haloalkyl, hydroxyl, hydroxy$(C_1-C_5)$alkyl, $(C_1-C_5)$alkoxy$(C_1-C_5)$alkyl, cyano, optionally substituted phenyl, optionally substituted benzyl, —COOR$_5$, —NR$_6$R$_7$, R$_5$OOC—$(C_1-C_5)$alkyl, NR$_6$R$_7$—$(C_1-C_5)$alkyl, —CONR$_6$R$_7$, NR$_6$R$_7$—CO—$(C_1-C_5)$alkyl, —SO$_2$NR$_6$R$_7$, and —NR$_6$—COR$_5$;

$R_5$ is hydrogen, $(C_1-C_5)$alkyl or $(C_3-C_6)$cycloalkyl; and $R_6$ and $R_7$, are independently hydrogen, $(C_1-C_5)$alkyl, $(C_3-C_6)$cycloalkyl, $(C_1-C_5)$alkylcarbonyl, hydroxymethyl$(C_1-C_5)$alkyl, $(C_1-C_5)$alkoxymethyl$(C_1-C_5)$alkyl, aryl or —SO$_2$—R$_5$, or $R_6$ and $R_7$, taken together with the nitrogen atom to which they are attached, form an optionally substituted heterocyclyl;

or a salt thereof, or an enantiomer or diastereoisomer thereof.

2. The compound according to claim 1, wherein:

$R_4$ is pyridyl, phenyl, or pyrazolyl;

or a salt, thereof, or an enantiomer or diastereoisomer thereof.

3. The compound according to claim 1, wherein:

---- is a double bond; and $R_4$ is phenyl or pyridyl;

or a salt thereof, or an enantiomer or diastereoisomer thereof.

4. The compound according to claim 1, wherein:

---- is a single bond; and $R_4$ is phenyl, pyridyl or pyrazolyl;

or a salt thereof, or an enantiomer or diastereoisomer thereof.

5. A process for preparing the compound according to claim 1, comprising reacting a compound of formula (IV):

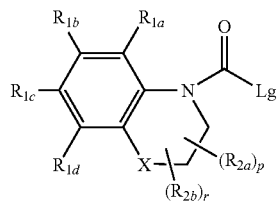

(IV)

wherein:
$R_{1a}$, $R_{1b}$, $R_{1c}$, $R_{1d}$, $R_{2a}$, $R_{2b}$, p and r are as defined in claim 1, and Lg is a leaving group;
with a compound of formula (V)

(V)

wherein:
$R_3$ and $R_4$ are as defined in claim 1.

6. A pharmaceutical composition, comprising the compound according to claim 1, or an enantiomer or diastereoisomer thereof, or a pharmaceutically acceptable salt thereof, in combination with at least one pharmaceutically acceptable excipient.

7. A pharmaceutical composition, comprising the compound according to claim 2, or an enantiomer or diastereoisomer thereof, or a pharmaceutically acceptable salt thereof, in combination with at least one pharmaceutically acceptable excipient.

8. A pharmaceutical composition, comprising the compound according to claim 3, or an enantiomer or diastereoisomer thereof, or a pharmaceutically acceptable salt thereof, in combination with at least one pharmaceutically acceptable excipient.

9. A pharmaceutical composition, comprising the compound according to claim 4, or an enantiomer or diastereoisomer thereof, or a pharmaceutically acceptable salt thereof, in combination with at least one pharmaceutically acceptable excipient.

* * * * *